United States Patent [19]
Hill et al.

[11] Patent Number: 5,411,744
[45] Date of Patent: May 2, 1995

[54] SILICONE VESICLES AND ENTRAPMENT

[75] Inventors: Randal M. Hill, Midland; Steven A. Snow, Sanford, both of Mich.

[73] Assignee: Dow Corning Corporation, Midland, Mich.

[21] Appl. No.: 254,855

[22] Filed: Jun. 6, 1994

Related U.S. Application Data

[62] Division of Ser. No. 212,753, Mar. 14, 1994, Pat. No. 5,364,633.

[51] Int. Cl.$^6$ ............................................. A61K 9/127
[52] U.S. Cl. .................................. 424/450; 428/402.2
[58] Field of Search ........................ 424/450; 428/402.2

[56] References Cited

PUBLICATIONS

Hill et al. Langmurr 9, 2789, 1993.

Primary Examiner—Gollamudi S. Kishore
Attorney, Agent, or Firm—James L. DeCesare

[57] ABSTRACT

A method of entrapping a water-soluble substance in vesicles formed from a siloxane surfactant is carried out by dissolving the substance to be entrapped in water, adding a siloxane surfactant, mildly agitating the mixture, and removing excess of water and substance. Water-insoluble substances can be entrapped in the vesicles by dissolving the substance to be entrapped in the siloxane surfactant, and mildly agitating the substance and the siloxane surfactant. Suitable siloxane surfactants are $R-[Si(Me)_2O]_{14}-Si(Me)_2-R$ in which R is $-(CH_2)_3(OCH_2CH_2)_7OH$, $R-[Si(Me)_2O]_{14}-Si(Me)_2-R$ in which R is $-(CH_2)_3(OCH_2CH_2)_{12}OH$, $Me_3SiO[Si(Me)_2O]_{22}-[SiMeRO]_2-SiMe_3$ in which R is $-(CH_2)_3(OCH_2CH_2)_{12}OH$, and $Me_3SiO[Si(Me)_2O]_{103}-[SiMeRO]_{10}-SiMe_3$ in which R is $-(CH_2)_3(OCH_2CH_2)_{12}OH$.

12 Claims, 1 Drawing Sheet 0.1 μm

SILICONE VESICLES AND ENTRAPMENT

This is a divisional of application Ser. No. 08/212753, filed on Mar. 14, 1994, now U.S. Pat. No. 5,364,633.

BACKGROUND OF THE INVENTION

This invention is directed to siloxane surfactants and to the formation of vesicles from siloxane surfactants. More particularly, the invention is directed to the use of vesicles formed from siloxane surfactants for the entrapment of water-soluble and water-insoluble substances.

The first problem to be solved by the present invention is to find a siloxane molecule which is able to form vesicles. The second problem to be solved by the present invention is to develop a use of such vesicles formed from siloxane surfactants for substance entrapment.

Because of the nature of the siloxane linkage, siloxane surfactants do not follow the usual rules of surfactant activity with regard to such things as aggregate formation and solubilization. Therefore, to even find a siloxane molecule which is able to form vesicles is quite surprising and unexpected. What is even more surprising and unexpected, is that having once pinpointed a particular siloxane molecule for vesicle formation, that the vesicle formed from the siloxane surfactant would also be useful to entrap substances.

The problems outlined above are solved according to the present invention, by the careful investigation and selection of only certain particular siloxane molecules which have been found to be capable of vesicle formation; and their use in substance entrapment.

The advantages and benefits to be derived by the use of siloxane surfactants in vesicle formation and substance entrapment, include the fact that siloxanes possess a non-hydrocarbon character, and therefore provide a different set of physical properties than is currently available with hydrocarbon-based surfactant molecules. Secondly, siloxane surfactants have been found to form vesicles "spontaneously" on contact with water, and therefore they eliminate the use of energy intensive processes such as sonification, which are required for non-siloxane based surfactants. Thirdly, because the siloxane backbone offers chemically reactive sites, it is possible to easily exploit the formation of polymerized vesicles.

DISCUSSION OF THE PRIOR ART

Aqueous dispersions of lipids in the form of particles having a lamellar structure, termed liposomes or vesicles, are excellent vehicles for the delivery or encapsulation of pharmaceutical substances. Handjani-Vila, et al. in the Int. J. Cosmetic Sci., 1 (1979) 303, in an article entitled "Dispersions of lamellar phases of nonionic lipids in cosmetic products", have demonstrated the advantages that can be obtained by the application of such systems to the skin, in particular to the use of nonionic lipids in aqueous dispersions. The synthetic nonionic lipids described by Handjani-Vila et al are used either alone, or as commonly practiced in combination with cholesterol or dicetylphosphate.

Handjani-Vila et al. showed that vesicles formed by nonionic lipids can form either a total cosmetic system alone, or a vehicle for water soluble active substances. As a cosmetic system, they facilitate the supply of lipids and water to the stratum corneum, and are able in the absence of a moisturizer to prevent the occurrence of dry skin. As a vehicle, they also effectively facilitate the transport of diverse substances such as moisturizers, tanning agents, and sunscreens, into the stratum corneum, and furthermore prevent subsequent elimination by water washing. These formulations were clearly less aggressive and more effective than conventional emulsion based lotions and creams.

In general terms, a lipid has bee defined, for example, in the "Dictionary of Colloid and Surface Science", by Becher & Dekker, New York, 1990, to be any one of a group of organic compounds, characterized by a greasy feel, insoluble in water, but soluble in a number of organic solvents, such as an alcohol or ether; or as a fat. However, in this context, lipid means more specifically the class of surface active lipids, for example, the phospholipids or lecithins, which are dispersible into water to form lamellar phase particles or liposomes.

Handjani-Vila et al also defined lipid to be a synthetic, tailor-made material of the structure $R—[O—CH_2—C(CH_2OH)H]_n—OH$ in which R is an alkyl group. These materials are said to be branched chain polyglycerol ethers. The advantage of such a synthetic material is the avoidance of considerable problems of reproducibility and stability arising from the use of lecithins.

Lautenschlager in Cosmetics & Toiletries, 105 (1990) 89, in an article entitled "Liposomes in dermatological preparations Part I", and in Cosmetics & Toiletries, 105 (1990) 63, in an article entitled "Liposomes in dermatological preparations Part II", expands the class of nonionic lipids which form vesicles to include ethoxylated fatty alcohols, and synthetic, linear or branched chain polyglycerol ethers with R being a linear or branched-chain saturated hydrocarbon residue such as hexadecyl. Lautenschlager also states that such nonionic lipids are usually formulated on a 1:1 basis with cholesterol or dicetyl phosphate, because they do not form vesicles on their own. Other bilayer forming amphiphiles or surfactants which form vesicles include dialkyl phosphates and N,N-dimethyl-N,N-dialkyl ammonium salts.

Liposomes are defined by Lautenschlager as spherical, globular, vesicles, the membranes of which consist of a bilayer of amphiphilic lipid molecules. Most cosmetic and pharmaceutical liposomes are composed of various phospholipids of natural, semi-synthetic and synthetic origin, with the major component being phosphatidylcholine. Minor components can include phosphatidylethanolamine, phosphatidylinositol, and phosphatidic acid.

The term vesicle refers to a structure consisting of a closed bilayer membrane envelope. Vesicles are often globular or tubular in shape but can be quite irregular. In the context of the present invention however, vesicles made using siloxane surfactants are not liposomes, because they are not actually prepared from materials recognized as lipids. A liposome is rather a specific type of vesicle prepared from lipid amphiphiles.

The manufacturing processes for vesicles as taught in the prior art depend on the use of high energy homogenizers and usually consist of two steps which are (1) mixing the amphiphile with water, followed by (2) making the vesicles uniform in size distribution. Excess water soluble substance outside the vesicles can be removed in a third step, but for cosmetic applications this third step is not necessary.

Lautenschlager discusses various mechanisms of action of liposomes in cosmetic and dermatological formulations, including their use as a transport system for other active ingredients, and their use as active materials. The latter use is a manifestation of the similarity between the lipids used to form the liposomes and the lipids which make up the bilayers of skin cell walls, which would not necessarily hold true for the siloxane surfactants of the present invention.

Some of the water insoluble substances of current interest for cosmetic vesicle delivery are vitamin E, retinoids, steroids, and other lipophilic actives. Water soluble natural moisturizing factors have been incorporated into the interior of vesicles by Lautenschlager, and Lautenschlager includes a range of potential uses of vesicles in cosmetic and dermatological formulations which exploit their unique properties.

As noted by Lautenschlager, the phase transition temperature, that is gel-to-fluid, is an important criteria in the selection of a basic liposomal formulation. One of the unique features of siloxane surfactants of the present invention however, is that the siloxane surfactants form vesicles without any such phase transition between 0–90 degrees Centigrade. This advantage of the present invention over the teaching in Lautenschlager allows formulators more flexibility with regard to processing temperatures and storage stability. This feature, advantage, and benefit, of the present invention is due to the low melting point of the methylated siloxane portion of the surfactant molecules of this invention.

The use of vesicles in cosmetics or dermatological formulations is limited by their compatibility with other components of the formulation, and this is indicated in Lautenschlager. In particular, the presence of other surfactants, ethanol, and propylene glycol, are known to interfere with the vesicles. For example, other surfactants often transform vesicles into mixed micelles. Lautenschlager however notes that some vesicle forming surfactants are more stable to these effects than others.

Since siloxane surfactants do not form mixed micelles with organic surfactants as readily as other organic surfactants, as noted by Hill in *Mixed Surfactant Systems*, Holland & Rubingh, ACS Symp. Ser., 501 (1992) 278, in an article entitled "Interactions between siloxane surfactants and hydrocarbon surfactants", it is reasonable to expect that vesicles formed from siloxane surfactants would be more tolerant of the presence of other surface active agents.

In the past, cosmetic products relied on simply combining moisturizing or cell regenerating agents with an emulsion or a cream base. However, cosmetic products have now reached the stage where liposomes can encapsulate active ingredients thought to be necessary for the skin, so that they may be applied directly to skin cells, as noted by Suzuki et al in *Cosmetics & Toiletries*, 105 (1990) 65, in an article entitled "The application of liposomes to cosmetics".

Suzuki et al teach that an important benefit of liposomal encapsulation is the enhanced transport of the active ingredient into the stratum corneum when encapsulated in a liposome. Thus, encapsulation for cosmetic uses not only has the objective of protecting the sensitive active, but of enhancing the transport of the active into the stratum corneum.

This effect relies on the similarity of the lipid bilayers of the liposome with those of the cell walls of the skin, and functions differently for the siloxane surfactant vesicles described in the instant invention. Such a difference represents a surprising and exploitable advantage for the siloxane surfactants according to the present invention. Thus, the physiology of the skin is not so simple that all questions regarding how and to which cells liposomes "fuse" in penetrating the skin barrier, can be answered with any certainty. Clearly the potential exists for vesicles formed from siloxane surfactants to present an entirely different behavior for the technologist to exploit, which constitutes another added advantage and benefit provided by this invention over the systems described in the prior art.

Suzuki et al. state that organic solvents are used in most liposome preparation methods. This creates a safety problem from solvent residues in the final product. Since no such solvent is required to efficiently form vesicles using siloxane surfactants, this represents another distinct and decided advantage for the instant siloxane technology.

Cosmetic-carrying liposomes can be prepared by a variety of techniques. All such techniques involve an intensive agitation or shear of aqueous suspensions of lipids by means of sonication, high pressure extrusion, or mixing of high pressure jets, as shown for example by Strauss in *J. Soc. Cosmet. Chem.*, 40 (1989) 51, in an article entitled "Liposomes: from theoretical model to cosmetic tool". Liposomes have become increasingly important as a vehicle for the controlled delivery of cosmetics. This development parallels the application of liposomes for drug delivery. Liposomes can encapsulate many types of cosmetic agents. Such encapsulation offers improved uptake, adhesion, and persistence of active ingredients in skin and hair products, and this is noted by Strauss. Strauss also outlines procedures for the preparation of liposomes by incorporating either water soluble or water insoluble active ingredients.

Mitchell et al. in the *J. C. S. Faraday Trans.* 2, 77 (1981) 601, in an article entitled "Micelles, vesicles and microemulsions"; and Israelachvili et al. in the *J. C. S. Faraday Trans* 2, 72 (1976) 1525, in an article entitled "Theory of self-assembly of hydrocarbon amphiphiles into micelles and bilayers"; each teach a method for calculating a so-called surfactant parameter "S" which quantifies the shape of the surfactant molecule. The numerical value of S is said to predict the type of aggregate micelle or vesicle the surfactant will prefer to form in an aqueous solution. Values of S between 0.5 and 1.5 are stated to indicate a tendency to form bilayer structures including vesicles.

This concept was derived for surfactants containing linear alkyl hydrophobic groups. Its application to the siloxane surfactants of the present invention, particularly the polymeric type, however, is not at all apparent; although Hill et al. in *Langmuir*, 9 (1993) 2789, in an article entitled "Lyotropic liquid crystal phase behavior of polymeric siloxane surfactants", provide procedures including bond lengths needed to apply this calculation to siloxane surfactants. The most preferred siloxane surfactant structures for forming vesicles are said to be those for which $0.5 \leq S \leq 1.5$, as calculated using the procedures of Hill et al.

Procedures for the preparation of large unilamellar vesicles from conventional phospholipid amphiphiles are shown by the patentee Papahadjopoulos in U.S. Pat. No. 4,078,052, which issued Mar. 7, 1978. The Papahadjopoulos procedure includes sonication, followed by an intricate manipulation of the solution using $Ca^{2+}$ ions and chelating agents. U.S. Pat. No. 4,078,052 illustrates the energy intensive and difficult procedures which must be used to prepare vesicles from phospholipids. Such procedures are not required however according to the present invention.

Talsma et al in *BioPharm*, October (1992) 36, in an article entitled "Liposomes as drug delivery systems, part I: preparation"; and in *Pharmaceutical Technology*, November (1992) 53, in an article entitled "Liposomes as drug delivery systems, part II: characterization"; and further in *Pharmaceutical Technology*, January (1993) 36, in an article entitled "Liposomes as drug delivery systems, part III: stabilization"; state that vesicles formed by phospholipid bilayers dispersed in aqueous media are used in cosmetics and dermatalogicals, and are potential carriers for diagnostic agents and pharmaceuticals.

A few of such liposome based parenteral and dermal drug formulations for human use are now on the market. In the near future, one can reasonably expect more liposomal formulations for the solubilization of lipophilic drugs, for active and passive drug targeting, for sustained release of drugs or proteins, and for antigen presentation; and all of these expectations are noted by Talsma et al.

But some unsolved problems related to large scale production, stabilization, and safety of liposomes, may hamper development of this type of technology. On the other hand, vesicles formed using the siloxane surfactants of the present invention offer a potential for overcoming these problems, because of the different physical properties and the distinctly non-lipid character of vesicles formed from siloxane surfactants.

In view of the above, the several significant advantages and benefits provided and derived according to the practice of the method of present invention should be more than apparent.

SUMMARY OF THE INVENTION

It is an object of the present invention to provide a method of entrapping a water-soluble substance in a vesicle formed from a siloxane surfactant. According to the method, a mixture is formed by dissolving the water-soluble substance to be entrapped in water, whereupon a siloxane surfactant is added to the mixture. The mixture is mildly agitated, and the excess of the water-soluble substance to be entrapped is removed from the mixture.

It is also an object of the present invention to provide a method of entrapping a water-insoluble substance in a vesicle formed from a siloxane surfactant. According to this method embodiment, the water-insoluble substance to be entrapped is dissolved in a siloxane surfactant, and the water-insoluble substance and the siloxane surfactant are mildly agitated.

It is a further object of the present invention to select a particular category and type of siloxane molecule enabled to form vesicles, and to utilize vesicles formed from the siloxane surfactants for entrapment of substances which are water-soluble and water-insoluble materials.

The advantages and benefits of the herein described present invention can be appreciated when it is considered that prior to the present invention, surfactants known to form vesicles were principally dialkyl cationic surfactants and phospholipids. There is no structural resemblance between these classes of organic surfactants and the siloxane surfactants employed herein.

Rather, the siloxane surfactants of the invention are polymeric molecules which can contain a wide variety of molecular species. It is surprising that such a polydisperse mixture would form a highly organized structure such as a vesicle. It is even more unexpected that complex molecules such as siloxane surfactants would pack themselves together into an orderly liquid crystalline state. In addition, because of the presence in the siloxane surfactant molecule of the $\equiv$Si—O—S$\equiv$ linkage, siloxane surfactants do not follow the usual patterns of surfactant activity.

While siloxane surfactants are useful in the manufacture of polyurethane foam, and as wetting agents and surface-feel modifiers, the capability of siloxane surfactants to also form vesicles for the entrapment of water-soluble and water-insoluble substances is unexpected. Comparable organic materials having similar uses are not known to possess the additional capability of vesicle formation and entrapment.

A principle benefit and advantage derived by the practice of the present invention is the facility with which the siloxane surfactants of the invention form vesicles. Prior to this invention, the formation of stable vesicles from known dialkyl cationic surfactants and phospholipids required very involved and special procedures including the necessity for high energy mixing in their preparation.

According to this invention, however, vesicles formed from siloxane surfactants can be formed with relative ease, and it is simply a matter of mixing the siloxane surfactant with water. Comparable organic polymers on the other hand which are not known to form vesicles require much more energy, time, and special procedural and processing steps, just to disperse them into a solution.

These and other features, objects, and advantages of the present invention will become more apparent from a consideration of the following detailed description thereof.

BRIEF DESCRIPTION OF THE DRAWING

The single FIG. 1 of the drawing is a cryo-TEM micrograph of a freshly prepared, ten percent solution of a siloxane surfactant having the formula R—[Si(Me)-2O]$_{14}$—Si(Me)$_2$—R wherein R is —(CH$_2$)$_3$(OCH$_2$CH$_2$)-$_{12}$OH in water at 20° C.

Figure 1:
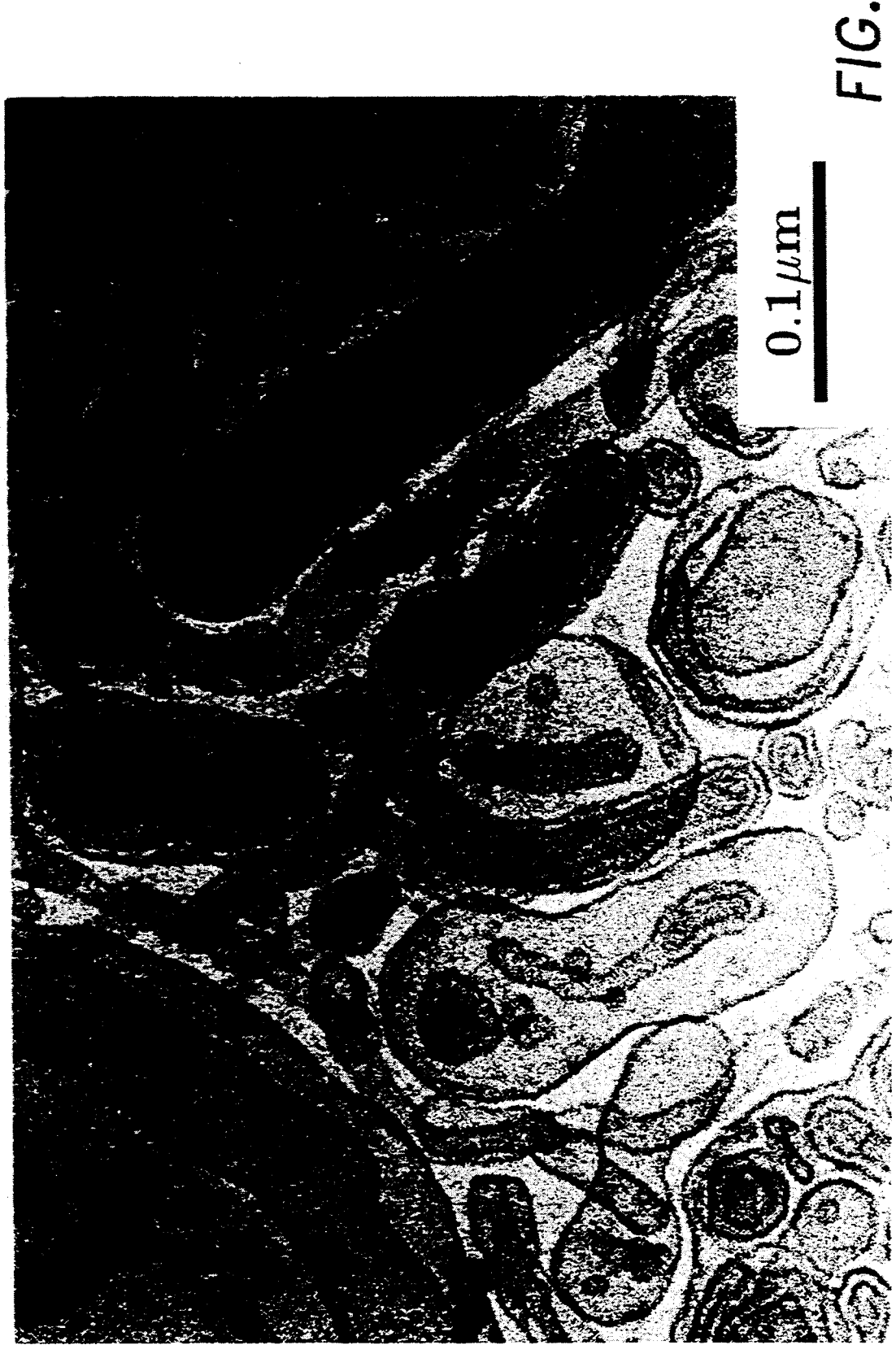
FIG. 1 demonstrates that this siloxane surfactant forms vesicles in water. It should be noted that the photograph shows many single and multi-walled large vesicles. In particular, this micrograph shows the presence of a variety of structures including unilamellar and multilamellar vesicles which range in shape from globular to long tubules. The variety of morphologies visible reflects the polydispersity of the siloxane surfactant.

The siloxane surfactant represented in FIG. 1 is one of the three siloxane surfactants set forth below in Examples I–III.

DETAILED DESCRIPTION OF THE INVENTION

Vesicles, sometimes referred to as liposomes, are surfactant molecules which form closed layered structures when dispersed in water. They are constructed of alternating layers of surfactant bilayers which are spaced by aqueous layers or compartments arranged in approximately concentric circles. If multilayered vesicles are subjected to ultrasound or vigorous agitation, the multilayered structure can be disrupted to produce a single bilayer assembly, which consists of a unilamellar vesicle in which a portion of the aqueous phase is entrapped within a single bilayer assembly. Typically, a vesicle has a diameter of 30 to 100 nanometers.

Vesicles are able to entrap within their assembly a portion of the aqueous phase present at the time of their formation. This provides a convenient vehicle for the inclusion within the vesicle of water-soluble substances. Water and hydrophilic compounds are entrapped in the central cavity of the vesicle between planes of the hydrophilic head groups. Water-insoluble substances can also be incorporated into the vesicle, although the water-insoluble substance locates itself between planes of the hydrophobic head groups of the vesicle system.

Among suitable examples of the various types of water-soluble substances which can be entrapped according to the invention are salicylic acid; Vitamin C; water-soluble deodorant substances; sodium stearate-based antiperspirant salts; water-soluble preservatives; water-soluble sunscreens; glycerine; enzymes; alpha-hydroxy substances such as glycolic acid; water itself; dyes such as VIOLET No. 2; and water-soluble drugs.

Among suitable examples of the various types of water-insoluble substances which can be entrapped according to the invention are Vitamin A; water-insoluble preservatives; water-insoluble sunscreens; water-insoluble drugs; pigment dispersions; and polydimethylsiloxane fluids.

Water-soluble substances are entrapped by dissolving the substance in water, forming and adding an appropriate siloxane surfactant, minimum agitation of the mixture by mild shaking for example, and removal of excess substance in the external phase by centrifugation, or by dialysis or size exclusion chromatography. Water-insoluble substances are entrapped by dissolving the substance in an appropriate siloxane surfactant, followed by minimum agitation of the mixture by mild shaking for example. No removal step by centrifugation, dialysis, or size exclusion chromatography, is required. A suitable co-solvent such as chloroform may be included however. The vesicle containing the entrapped water-insoluble substance can then be used by dispersing it in an aqueous system, if desired.

The siloxane surfactants of this invention have been found to form vesicles when used in low concentration levels up to concentration levels at or near the lower boundary of the lamellar liquid crystal phase. Thus, according to the present invention, the siloxane surfactants are employed in an amount of from 0.1 percent by weight to 40.0 percent by weight, preferably in a range of from 0.5 to 20.0 percent by weight. The water-soluble substance which is to be entrapped in the vesicles formed from these siloxane surfactants is employed in an amount of from 0.1 percent by weight to 10.0 percent by weight, with the balance of the composition being water. The water-insoluble substance which is to be entrapped in the vesicles formed from these siloxane surfactants is likewise employed in an amount of from 0.1 percent by weight to 10.0 percent by weight, with the balance of the composition being a suitable co-solvent such as chloroform.

Siloxane surfactant compounds for the formation of vesicles according to this invention can be represented by the organosilicon compounds having one of the following formulas:

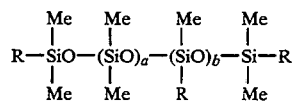

ABA/COMB

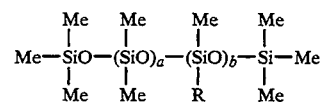

COMB

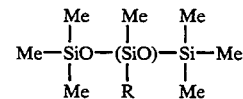

TRISILOXANE

In formulas (I) to (III) above, Me is the methyl group. R is a radical which can be methyl, $-(CH_2)_xO(C_2H_4O)_y(C_3H_6O)_zR'$, or $-(CH_2)_xN^+R_3''A^-$, with the proviso that at least one R radical in the molecule cannot be a methyl radical. R' is either hydrogen, a methyl radical, or an acyl radical. R'' is an alkyl radical having from one to six carbon atoms, a phenyl radical, a benzyl radical, or the radical $-CH_2CH_2OH$. The counterion $A^-$ is chloride, bromide, iodide, cyanide, a methyl sulfate radical, a salicylate radical, or a dodecylsulfate radical.

In formulas (I) and (II), a has a value of 0 to 200; b has a value of 0 to 50; with the proviso that a and b cannot both be zero. In formulas (I) to (III), x has a value of 3 to 6; y has a value of 4 to 30; and z has a value of 0 to 5.

The following four siloxane surfactants were formed into vesicles according to the present invention, and are representative of the types of organosilicon compounds set forth in the above generic formulas: $R-[Si(Me)_2O]_{14}-Si(Me)_2-R$ in which R is $-(CH_2)_3(OCH_2CH_2)_7OH$, $R-[Si(Me)_2O]_{14}-Si(Me)_2-R$ in which R is $-(CH_2)_3(OCH_2CH_2)_{12}OH$, $Me_3SiO[Si(Me)_2O]_{22}-[SiMeRO]_2-SiMe_3$ in which R is $-(CH_2)_3(OCH_2CH_2)_{12}OH$, and $Me_3SiO[Si(Me)_2O]_{103}-[SiMeRO]_{10}-SiMe_3$ in which R is $-(CH_2)_3(OCH_2CH_2)_{12}OH$. In these formulas, Me is the methyl radical.

The following examples are set forth for the purpose of illustrating the invention in more detail.

EXAMPLE I

Vesicles were prepared from siloxane surfactants, and their entrapping efficiency was evaluated. Three (3) different siloxane surfactant molecules were employed which corresponded to the compounds $Me_3SiO[Si(Me)_2O]_{22}-[SiMeRO]_2-SiMe_3$, $R-[Si(Me)_2O]_{14}-Si(Me)_2-R$, and $Me_3SiO[Si(Me)_2O]_{103}-[SiMeRO]_{10}-SiMe_3$. In all three of these siloxane surfactants, R was $-(CH_2)_3(OCH_2CH_2)_{12}OH$. There was initially prepared two milliliters of a two weight percent solution of each siloxane surfactant in a buffer solution containing 60 mM calcein which is a water-soluble fluorescent dye. Calcein, known as Fluorexon, is {bis[N,N-bis(carboxymethyl)-aminomethyl]fluorescein. At the concentration employed, the calcein dye was self-quenching and not fluorescent, and the three solutions were brown in color. Each solution contained vesicles formed from a siloxane surfactant entrapping a fraction of the solution volume in an excess of the solution. The calcein dye was removed from the solution external to the vesicles by size exclusion chromatographic separation using a SEPHADEX ® column, and also by ultracentrifugation. Once the calcein dye external to the vesicles had been removed, any leakage of the dye out of the vesicle was detectable, because the calcein dye became fluorescent in the lower concentration of the environment external of the vesicle. The leakage rate was accordingly quantified by monitoring fluorescence as a function of time.

EXAMPLE II

One-half of each of the solutions prepared in Example I was ultracentrifuged at 40,000 rpm (150,000 G) for thirty minutes. A small brown pellet of vesicles formed from the siloxane surfactant was visible in the bottom of each of the three solutions. The supernatant liquid was poured off, and the vesicles were redispersed in a fresh buffer solution, and again ultracentrifuged under the conditions noted above. Again a small brown pellet appeared at the bottom of each of the three solutions. Once more, the supernatant liquid was poured off, and the vesicles were once again redispersed in a fresh buffer solution. The solutions each appeared to be light brown in color, which indicated the presence of vesicles entrapping the concentrated calcein dye solution. Fluorescence increased very slowly which indicated that the vesicles formed from the siloxane surfactant did not leak rapidly. The addition of twenty microliters of a ten percent by weight solution of sodium dodecylsulfate (SDS) dissolved the vesicles, and caused a sudden and dramatic rise in fluorescence, which demonstrated conclusively that entrapment had occurred for each of the three siloxane surfactants. The entrapped volume was determined with the aid of a standardization curve for calcein dye.

EXAMPLE III

The other one-half of each of the three solutions prepared in Example I was passed twice through a small pre-packed size exclusion SEPHADEX ® column, and a cloudy middle fraction was collected. The solutions were washed through the column using an iso-osmotic buffer solution. SEPHADEX ® is a trademark of the Pharmacia Biotechnology Group of Piscataway, N.J., and is a dry insoluble powder column packing composed of microscopic beads that are synthetic organic compounds derived from the polysaccharide dextran. The dextran chains are crosslinked to provide a three-dimensional network, and functional ionic groups are attached to the glucose units of the polysaccharide chains by ether linkages. In the SEPHADEX ® size exclusion column, small calcein dye molecules "visit" the holes in the SEPHADEX ® column packing, and therefore pass through the column at a much slower rate than the vesicles formed from the siloxane surfactant. Following treatment of the solutions in the SEPHADEX ® column, the solutions each appeared to be light brown in color, which indicated the presence of vesicles formed from a siloxane surfactant entrapping the original concentrated calcein dye solution. Fluorescence increased very slowly which indicated that the vesicles did not leak rapidly. The addition of twenty microliters of a ten percent by weight solution of sodium dodecylsulfate (SDS) dissolved the vesicles, and caused a sudden and dramatic rise in fluorescence, which demonstrated conclusively that entrapment had occurred for each of the three siloxane surfactants. The entrapped volume was determined with the aid of a standardization curve for calcein dye.

The following additional example is set forth for the purpose of further illustrating the invention in more detail, and in order to provide more evidence of entrapment of materials with a siloxane surfactant.

EXAMPLE IV

A siloxane surfactant having the formula $R-[Si(Me)_2O]_{14}-Si(Me)_2-R$ in which R is $-(CH_2)_3(OCH_2CH_2)_7OH$, was added to an aqueous solution of Bromocresol Purple dye at a pH of about four. Bromocresol Purple is 5',5''-dibromo-o-cresol-sulfonephthalein. The acid form of Bromocresol Purple dye has a dark purple color while the base form has a bright yellow color. Vesicles formed in the solution and were observed under a microscope. The microscope was a Zeiss "Axioskop" optical microscope with Differential Interference Contrast optics. The microscope was equipped for photography of images and for realtime on-screen television viewing including video recording capability. The microscope is capable of detecting vesicles down to about 200 nanometers in size when equipped with a 100X oil-immersion lens at a 1250X total magnification. The vesicles were observed with the microscope, and a purple color was seen both on the outside and on the inside of the vesicles. When a sodium hydroxide solution was injected into the sample, an instantaneous color change was observed. The diffusion of sodium hydroxide was tracked by observing a yellow color front. When the yellow color front contacted a vesicle and surrounded it, the purple color on the inside of the vesicle remained for one to two minutes and slowly turned to yellow. This indicated that the vesicle formed from the siloxane surfactant acted as a barrier to the diffusion of sodium hydroxide, and that Bromocresol Purple was trapped within the vesicle. It further indicated that the rate of diffusion of sodium hydroxide across the vesicle was rapid.

Other variations and modifications may be made in the compounds, compositions, and methods described herein, without departing from the essential features and concepts of the present invention.

The forms of the invention described herein are exemplary only and are not intended as limitations on the scope of the invention as defined in the appended claims.

That which is claimed is:

1. A composition comprising a water-soluble substance entrapped in a vesicle formed from 0.1 to 40.0 percent by weight of a siloxane surfactant, the vesicle being formed by dissolving 0.1 to 10.0 percent by weight of the substance to be entrapped in water, adding the siloxane surfactant, and mildly agitating the mixture, the siloxane surfactant being an organosilicon compound having a formula selected from the group consisting of:

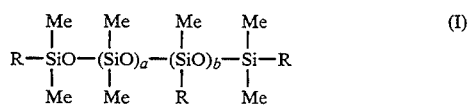

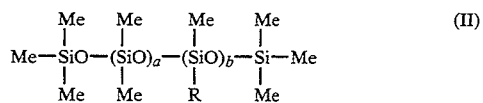

and

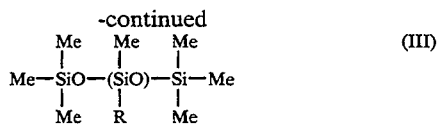

wherein Me is the methyl group; R is a radical selected from the group consisting of methyl, —(CH$_2$)$_x$O(C$_2$H$_4$O)$_y$(C$_3$H$_6$O)$_z$R', and —(CH$_2$)$_x$N$^+$R$_3$''A$^-$, with the proviso that at least one R radical in the molecule cannot be a methyl radical; R' is selected from the group consisting of hydrogen, a methyl radical, and an acyl radical; R'' is selected from the group consisting of alkyl radicals having from one to six carbon atoms, a phenyl radical, a benzyl radical, and the radical —CH$_2$CH$_2$OH; A$^-$ is a counterion selected from the group consisting of chloride, bromide, iodide, cyanide, a methyl sulfate radical, a salicylate radical, and a dodecylsulfate radical; a has a value of 0 to 200; b has a value of 0 to 50; with the proviso that a and b cannot each be zero; x has a value of 3 to 6; y has a value of 4 to 30; and z has a value of 0 to 5.

2. A composition according to claim 1 in which the siloxane surfactant has the formula:

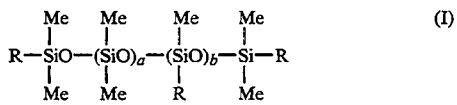

in which Me, R, a, and b, have the same meaning as in claim 1.

3. A composition according to claim 1 in which the siloxane surfactant has the formula:

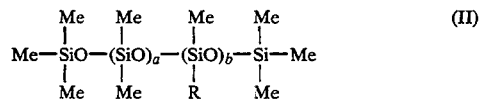

in which Me, R, a, and b, have the same meaning as in claim 1.

4. A composition according to claim 1 in which the siloxane surfactant has the formula:

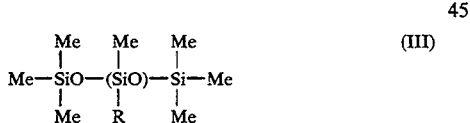

in which Me and R have the same meaning as in claim 1.

5. A composition according to claim 1 in which the siloxane surfactant is a compound having a formula selected from the group consisting of: R—[Si(Me)$_2$O]$_{1-4}$—Si(Me)$_2$—R in which R is —(CH$_2$)$_3$(OCH$_2$CH$_2$)$_7$OH, R—[Si(Me)$_2$O]$_{14}$—Si(Me)$_2$—R in which R is —(CH$_2$)$_3$(OCH$_2$CH$_2$)$_{12}$OH, Me$_3$SiO[Si(Me)$_2$]$_{22}$—[SiMeRO]$_2$—SiMe$_3$ in which R is —(CH$_2$)$_3$(OCH$_2$CH$_2$)$_{12}$OH, and Me$_3$SiO[Si(Me)$_2$O]$_{103}$—[SiMeRO]$_{10}$—SiMe$_3$ in which R is —(CH$_2$)$_3$(OCH$_2$CH$_2$)$_{12}$OH, and Me is the methyl radical.

6. A composition according to claim 1 in which the water-soluble substance is selected from the group consisting of salicylic acid, Vitamin C, glycerine, enzymes, glycolic acid, and VIOLET No. 2.

7. A composition comprising a water-insoluble substance entrapped in a vesicle formed from 0.1 to 40.0 percent by weight of a siloxane surfactant, the vesicle being formed by dissolving 0.1 to 10.0 percent by weight of the substance to be entrapped in water, adding the siloxane surfactant, and mildly agitating the mixture, the siloxane surfactant being an organosilicon compound having a formula selected from the group consisting of:

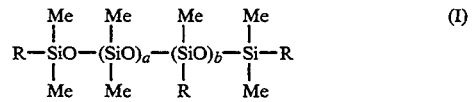

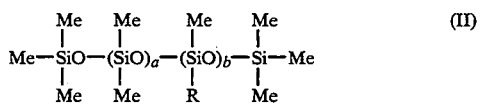

and

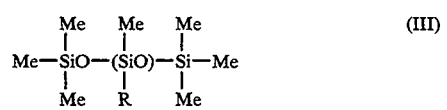

wherein Me is the methyl group; R is a radical selected from the group consisting of methyl, —(CH$_2$)$_x$O(C$_2$H$_4$O)$_y$(C$_3$H$_6$O)$_z$R', and —(CH$_2$)$_x$N$^+$R$_3$''A$^-$, with the proviso that at least one R radical in molecule cannot be a methyl radical; R' is selected from the group consisting of hydrogen, a methyl radical, and an acyl radical; R''is selected from the group consisting of alkyl radicals having from one to six carbon atoms, a phenyl radical, a benzyl radical, and the radical —CH$_2$CH$_2$OH; A$^-$ is a counterion selected from the group consisting of chloride, bromide, iodide, cyanide, a methyl sulfate radical, a salicylate radical, and a dodecylsulfate radical; a has a value of 0 to 200; b has a value of 0 to 50; with the proviso that a and b cannot each be zero; x has a value of 3 to 6; y has a value of 4 to 30; and z has a value of 0 to 5.

8. A composition according to claim 1 in which the siloxane surfactant has the formula:

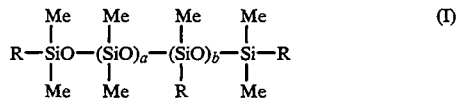

in which Me, R, a, and b, have the same meaning as in claim 7.

9. A composition according to claim 7 in which the siloxane surfactant has the formula:

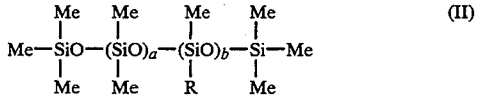

in which Me, R, a, and b, have the same meaning as in claim 7.

10. A composition according to claim 7 in which the siloxane surfactant has the formula:

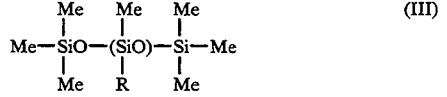

in which Me and R have the same meaning as in claim 7.

11. A composition according to claim 7 in which the siloxane surfactant is a compound having a formula selected from the group consisting of: R—[Si(Me)$_2$O]$_{1-14}$—Si(Me)$_2$—R in which R is (CH$_2$)$_3$(OCH$_2$CH$_2$)$_7$OH, R—[Si(Me)$_2$O]$_{14}$—Si(Me)$_2$—R in which R is (CH$_2$)$_3$(OCH$_2$CH$_2$)$_{12}$OH, Me$_3$SiO[Si(Me)$_2$O]$_{22}$—[SiMeRO]$_2$—SiMe$_3$ in which R is —(CH$_2$)$_3$(OCH$_2$CH$_2$)$_{12}$OH, and Me$_3$SiO[Si(Me)$_2$O]$_{103}$—[SiMeRO]$_{10}$—SiMe$_3$ in which R is —(CH$_2$)$_3$(OCH$_2$CH$_2$)$_{12}$OH, and Me is the methyl radical.

12. A composition according to claim 7 in which the water-insoluble substance is selected from the group consisting of Vitamin A, pigments, and polydimethylsiloxane.

* * * * *